(12) United States Patent
Stamler

(10) Patent No.: US 6,299,617 B1
(45) Date of Patent: *Oct. 9, 2001

(54) INSTRUMENT FOR FIXATING THE EYE DURING CATARACT SURGERY

(76) Inventor: John Stamler, 540 E. Jefferson St., Iowa City, IA (US) 52245

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/050,587

(22) Filed: Mar. 30, 1998

(51) Int. Cl.[7] .............................. A61B 17/24; A61B 17/26
(52) U.S. Cl. ............................ 606/107; 600/236
(58) Field of Search .................. 606/1, 107, 166; 600/236, 201

(56) References Cited

U.S. PATENT DOCUMENTS

| | | | |
|---|---|---|---|
| 2,033,397 | * 3/1936 | Richman | 606/50 |
| 3,490,455 | 1/1970 | Illig . | |
| 4,275,733 | 6/1981 | Marinoff . | |
| 4,579,116 | * 4/1986 | Catalano | 128/303 |
| 4,773,415 | * 9/1988 | Tan | 128/303 |
| 4,991,567 | 2/1991 | McCuen, II et al. . | |
| 5,174,279 | 12/1992 | Cobo et al. . | |
| 5,224,950 | * 7/1993 | Prywes | 606/166 |
| 5,320,113 | * 6/1994 | Tan | 128/858 |
| 5,411,510 | * 5/1995 | Fugo | 606/166 |
| 5,451,230 | * 9/1995 | Steinert | 606/107 |
| 5,556,417 | 9/1996 | Sher . | |
| 5,653,725 | * 8/1997 | Simon et al. | 606/190 |
| 5,662,668 | 9/1997 | Kurwa . | |
| 5,676,679 | 10/1997 | Simon et al. . | |
| 5,695,492 | * 12/1997 | Brown | 606/4 |
| 5,752,960 | * 5/1998 | Nallakrishnan | 606/107 |
| 6,086,602 | * 7/2000 | O'Donnell, Jr. | 606/166 |

* cited by examiner

Primary Examiner—Richard K. Seidel
Assistant Examiner—Jennifer Maynard
(74) Attorney, Agent, or Firm—Simmons, Perrine, Albright & Ellwood PLC

(57) ABSTRACT

A method and apparatus for fixating an eye during ocular surgery, including inserting a two-pronged tool through an incision in the cornea into the anterior chamber. The two prongs prohibit movement of the eye in all directions. An alternate embodiment provides for use of two such two-pronged tools which are coupled together and each of the two-pronged tools is inserted in the incision and help to prohibit movement of the eye.

17 Claims, 4 Drawing Sheets

INSTRUMENT FOR FIXATING THE EYE DURING CATARACT SURGERY

BACKGROUND OF THE INVENTION

The present invention pertains to instruments for fixating the eye during ocular surgery such as cataract extraction by the small incision technique, commonly known as Phacoemulsification or Phaco technique and other operations of the anterior segment of the eye that are performed under local anesthesia.

In recent years, two surgical techniques for removing a cataract from the eye are employed. The large incision technique and the small incision or Phaco technique.

In the large incision technique, an incision (approximately 8–10 mm), almost half of the circumference of the cornea is made, and the cataract is expressed or squeezed out of the eye manually. The advantage with this technique is that it is much easier to perform. The disadvantages are the longer time to recuperate, and it produces more astigmatism.

In the small incision or Phaco technique, a small incision, approximately three (3) mm long is made on the peripheral margin of the cornea (usually temporal). Then a needle or sharp forceps is used to puncture the anterior lens capsule and tear a circular opening (capsulorhexis) to create access to the cataractous lens cortex and nucleus through the corneal incision and capsular opening. An ultrasonic cutting tip is then inserted inside the eye to remove the cataract. The advantages with this technique are the stronger wound, faster recuperation, and less astigmatism.

Ophthalmologists have continued to improve the Phaco technique. One such improvement is the recent change from needle-block anesthesia injections which paralyze the eye to a topical anesthesia, administered through eye drops. The eye drops eliminate the swelling, bruising, discomfort and trauma to the tissues around the eye which are often associated with needle-block anesthesia injections and further eliminates the possible complication of inadvertent ocular perforation from the anesthetic needle.

While the topical anesthesia has many beneficial aspects, including freedom of movement immediately after the completion of the Phaco procedure, it also allows the undesirable free movement of the eye during the surgical procedure.

Ophthalmologists have often used three different approaches to fixate the eye under such circumstances. One has been to use a toothed ring that extends around the perimeter of the cornea which is pressed down into the sclera. Another approach has been to use forceps to grab the outside of the eye to restrict movement. Alternatively, it is possible to use a special diamond knife to hold the eye steady after one of the two incisions is made.

While these approaches have been used in the past, each has serious drawbacks. The toothed ring requires an increased pressure in the eye when the surgeon presses the ring into the sclera. During the part of the operation where the anterior capsule is torn open (capsulorhexis), the increased intraocular pressure makes the procedure more difficult and increases the likelihood of a complication. The approach using forceps to restrain eye movement has the drawback that the forceps on occasion accidentally release the eye because it is difficult to grasp the eye firmly, or in other situations, tear blood vessels and cause bleeding.

Using the knife to hold the eye prevents movement in three directions (to either side or toward the handle), but not in the fourth direction—toward the point of the knife. The two other drawbacks of the diamond knife are the expense of the instrument and the difficulty of reinsertion after removal. It is difficult to reinsert the blade in the same incision without creating a new cut.

Consequently, there is a need for improvement in instruments and methods for fixating the eye during cataract surgery.

SUMMARY OF THE INVENTION

It is an object of the present invention to provide a method and apparatus for restraining eye movement during intraocular surgery.

It is a feature of the present invention to include a multi-pronged eye restraining tool.

It is an advantage of the present invention to provide for restraining eye movement in all directions.

It is another feature of the present invention to deploy the multi-pronged tool in the paracentesis site or side port of a Phacoemulsification surgery or other anterior segment surgery.

It is another advantage of the present invention to limit the additional trauma or side effects associated with eye fixation.

The present invention is a method and apparatus for restraining eye movement during ocular surgery which is designed to satisfy the aforementioned needs, provide the previously stated objects, include the above-listed features and achieve the already articulated advantages.

Accordingly, the present invention includes an apparatus having a handle member, a longitudinal shaft coupled to the handle member, a first protuberance coupled to the shaft member for insertion through an incision in the eye, the first protuberance extending in a first direction from the shaft member, a second protuberance coupled to the shaft member at a predetermined distance from the first protuberance and extending in a second direction from the shaft member, the second protuberance for restricting the penetration of the first protuberance into the eye.

BRIEF DESCRIPTION OF THE DRAWINGS

The invention may be more fully understood by reading the foregoing description of the preferred embodiments of the invention, in conjunction with the appended drawings wherein.

DETAILED DESCRIPTION OF THE DRAWINGS

Figure 1:
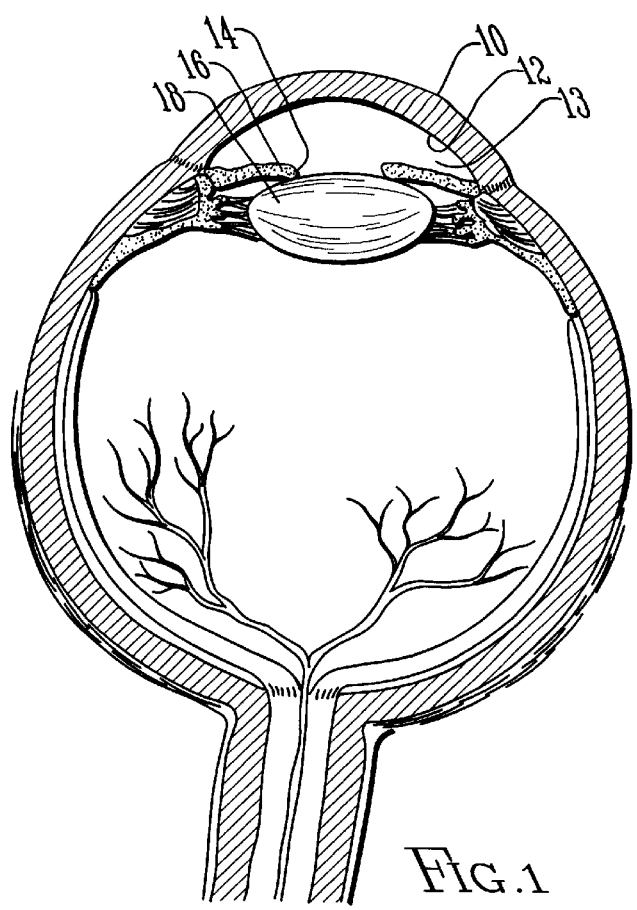
FIG. 1 is a cross-sectional view of an eye showing the important parts during cataract surgery.

Now referring to the drawings, where like numerals refer to like matter throughout, and more particularly to FIG. 1, there is shown a cross-sectional view of a typical human eye. The front part of the eyeball is a clear transparent structure called the cornea IO. The back surface of the cornea is lined with a layer known as the endothelium 12. The endothelium borders the anterior chamber 13. Posterior to the cornea, endothelium, and anterior chamber is the iris 16, the colored part of the eye (brown, blue or green eyes). The opening in the center of the iris is the pupil 14. Behind the iris is the lens 18 of the eye. A thin capsule surrounds the lens. The side toward the cornea is called anterior capsule. A normal lens is clear and transparent. However, if the lens 18 becomes cloudy or opaque, as in old age, it is often called a cataract, and surgery is used to remove and replace this lens with a clear artificial lens called an intraocular lens implant.

Figure 2:
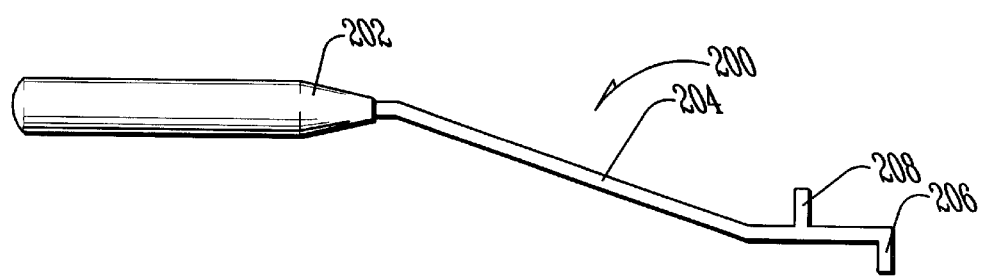
FIG. 2 is a perspective view of the apparatus of the present invention.

Now referring to FIG. 2, there is shown a perspective view of the multi-pronged apparatus of the present invention generally designated 200, having a handle 202 and an elongated shaft 204 coupled to the handle, and distal to the handle are protuberances 206 and 208.

Preferably, the shaft member 204 and the protuberances 206 and 208 are constructed of a single piece of surgical steel or titanium with the handle 202 being attached thereto. In some circumstances, the entire device 200 will be constructed of a single piece of surgical steel or titanium. Handle 202 is shown as a device which is intended to be gripped by a medical professional; however, in an alternate embodiment, handle 202 could be a sleeve, into which a finger is inserted, or any means of strapping or other coupling the tool to a human hand could be substituted.

Figure 3:
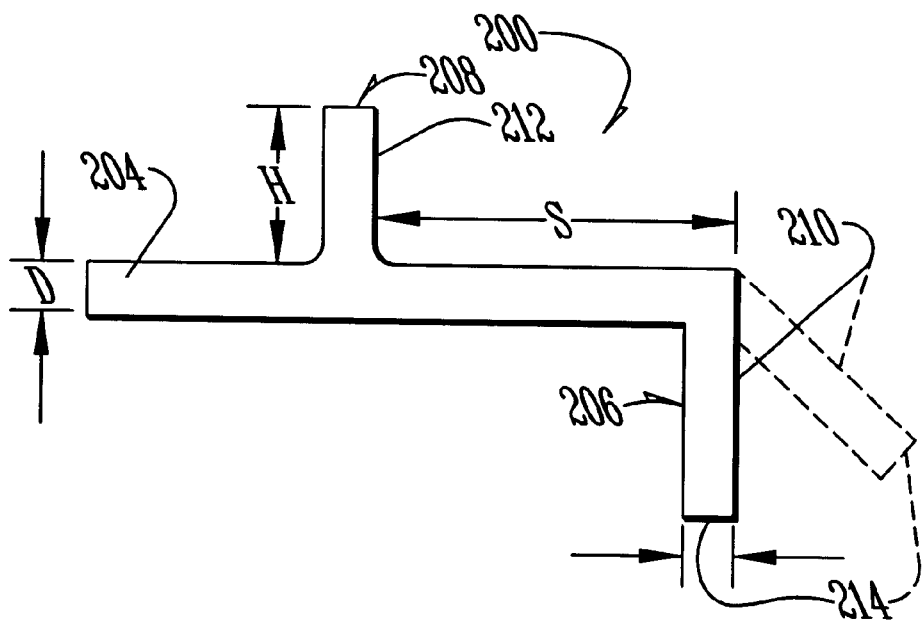
FIG. 3 is a plan view of the apparatus of the present invention.

Now referring to FIG. 3, there is shown the distal portion of the apparatus 200 of the present invention which includes a portion of the distal portion of the elongated shaft 204; it also shows a first protuberance 206 and a second protuberance 208. The apparatus 200 is shown having a constant width dimension D which is typically somewhere between 0.1 mm and 1.5 mm, but preferably is approximately 0.5 mm in width. The height of protuberances 206 and 208 are a matter of design choice; however, the height of protuberance 206 is preferably on the order of 0.7 mm while the height of protuberance 208, which is dimension H, is preferably on the order of 1.2 mm. The separation of the leading edge 210 of protuberance 206 from the leading edge 212 of the protuberance 208, which is dimension S, is preferably on the order of 2 mm.

In an alternate embodiment, the protuberance 206 will extend from the elongated shaft 204 at an angle larger than 90° so that the protuberance tip 214 extends further from the handle 202 (FIG. 2) than if the protuberance had been at a 90° angle. This provides for a variable separation s' between the leading edge 210' and the leading edge 212.

Figure 4:
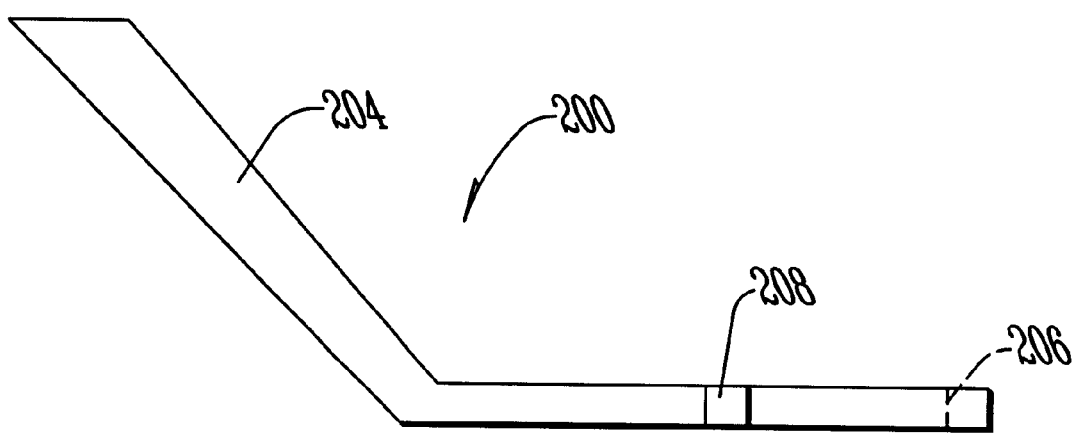
FIG. 4 is an elevational view of the apparatus of the present invention.

Now referring to FIG. 4, there is shown an elevational view of the apparatus of the present invention generally designated 200, which shows the shaft member 204, first protuberance 206 and second protuberance 208.

Figure 5:
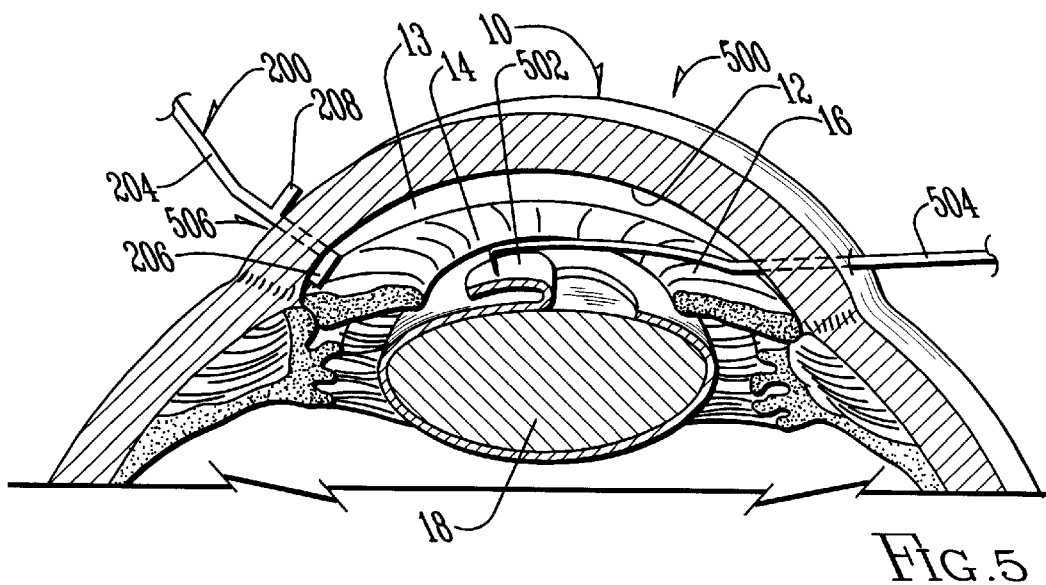
FIG. 5 is an enlarged sectional view of a portion of the eye with the apparatus of the present invention disposed therein in accordance with the procedure of the present invention.

Now referring to FIG. 5, there is shown an enlarged sectional view of a portion of the eye generally designated 500 with the apparatus of the present invention 200 disposed in the eye in accordance with the present invention. The anterior lens capsule 502 is shown to be partially opened with a bent needle (cystotome) 504 as the eye is shown to be fixated by the apparatus of the present invention 200. The invention's greatest utility is often during the step when the anterior capsule is opened. The apparatus 200 of the present invention is shown inserted through a separate incision 506 often referred to as a side port incision through the peripheral cornea. Protuberance 206 at the distal end of shaft member 204 is inserted through the side port incision 506 and enters the anterior chamber. Protuberance 208 restricts the protuberance 206 from extending too far into the anterior chamber. In operation, the surgeon or an assistant to the surgeon will insert the device 200, including protuberance 206, through the incision and may choose to rotate the device 200 so that the direction of the first protuberance is perpendicular to the longest dimension of the incision or sliding the device 200 along a length of the incision, thereby allowing for a more firm contact between the protuberance 206 and the edge of the corneal incision. The surgeon or assistant to the surgeon may then manually restrain eye movement by applying a slight outwardly pressure and/or by firmly holding the handle 202 (not shown). The length and position of the incision is a matter of choice by the surgeon, and it may be made in and through other sections of the eye.

Figure 6:
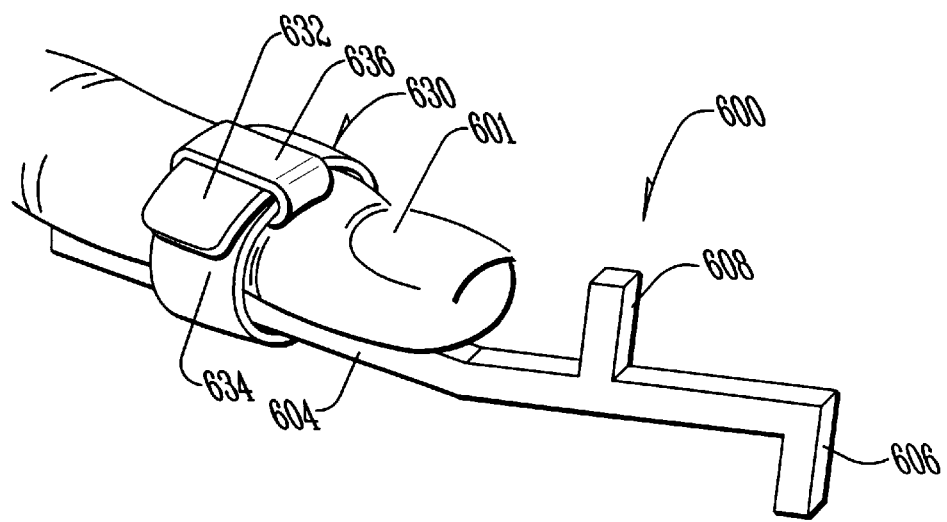
FIG. 6 is a perspective view of the apparatus of the present invention which is strapped to a human finger.

Now referring to FIG. 6, there is shown a perspective view of an apparatus of the present invention generally designated 600, which is attached to a human finger 601. Apparatus 600 includes a shaft 604, having a first protuberance 606 and a second protuberance 608, which are similar in arrangement and construction to shaft 204 and protuberance 206 and 208 of FIG. 2. Shaft 604 is coupled to a human finger 601 by strapping apparatus 630 which includes a strap having a first end 632 and a second end 634. Preferably a fastener of some type is used in area 636. The fastener in area 636 is preferably a Velcro fastener, but any other suitable fastener such as adhesives, snaps, buttons, ties could be substituted.

Figure 7:
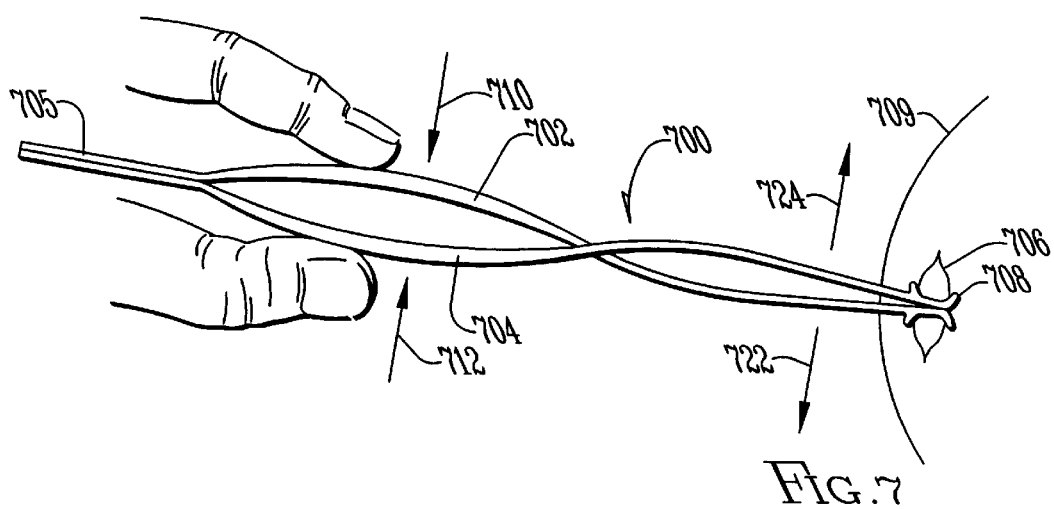
FIG. 7 is a perspective view of an alternate apparatus of the present invention showing such apparatus in use where the solid line arrows show the direction of force applied by the operator's fingers and the dashed line arrows show the direction of force and direction of movement of the apparatus within the eye.

Now referring to FIG. 7, there is shown a perspective view of an alternate apparatus of the present invention generally designated 700, which includes a first eye gripping member 702 and a second eye gripping member 704. Members 702 and 704 are preferably joined together at proximal end 705 and are capable of distension when a force is applied by the operator's fingers in a first direction 710 and a second direction 712. When force is applied in directions 710 and 712, members 702 and 704 are thereby caused to move in directions 722 and 724 respectively. Apparatus 700 is also shown having a distal end 708 which is inserted into a human eye 709 through a side port incision 706.

Figure 8:
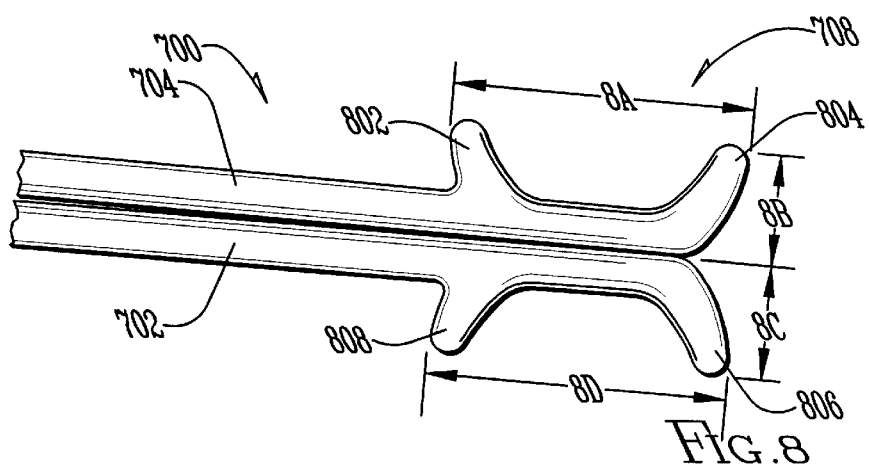
FIG. 8 is an enlarged view of the distal end of the apparatus of FIG. 7.

Now referring to FIG. 8, there is shown an enlarged view of the distal end 708 of the apparatus 700 of FIG. 7. Member 704 is shown having a top proximal protuberance 802 and a top distal protuberance 804 which are separated by a distance 8A which is preferably on the order of 1.5 mm. Top distal protuberance 804 is shown having a height dimension 8B which is preferably on the order of 0.25 mm. Member 702 is shown having a bottom proximal protuberance 808 and a bottom distal protuberance 806 which are separated by a distance 8D which is preferably similar to the distance 8A. Similarly, distance 8C representing the height dimension of bottom distal protuberance 806 is preferably similar to the distance 8B.

Figure 9:
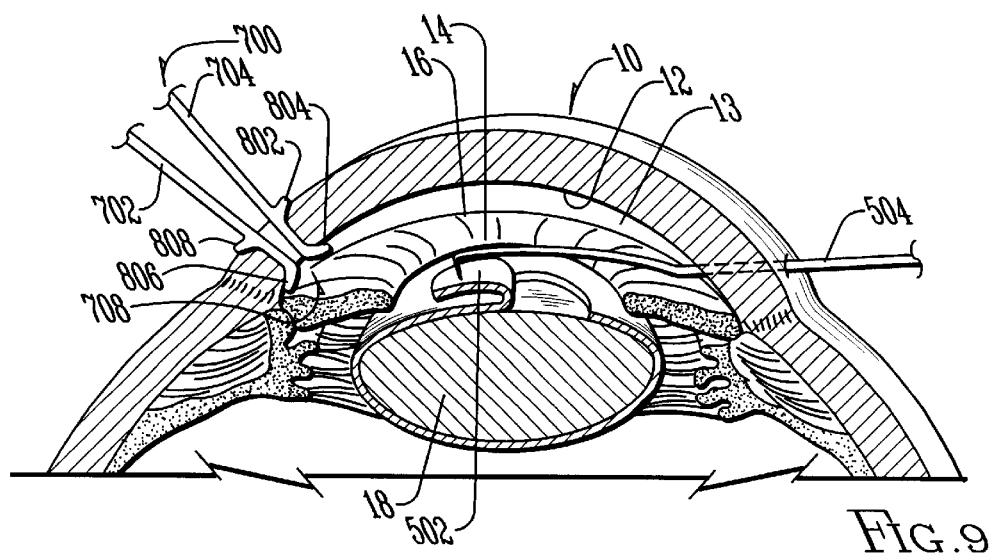
FIG. 9 is a perspective view of the apparatus of FIG. 7 disposed in a side port incision in a human eye.

Now referring to FIG. 9, there is shown a perspective view of the apparatus 700 disposed in a side port incision during an operation.

Now referring to FIGS. 7–9, it can be seen that the distal ends of the members 704 and 702 are caused to separate and more firmly engage the cornea 10 when the apparatus 700 is inserted in a side port incision during an operation and the members 702 and 704 are pressed in directions 710 and 712 by the physician.

The apparatus 700 is preferably made of material similar to apparatus 200 of FIG. 2. However, it is understood that the desire for flexing the members and biasing the members either toward a closed distal end or an open distal end may result in different choices of material, dimensions, coupling and biasing techniques all of which are well known in the art.

Throughout this description, cataract surgery has been used merely as an example of a type of surgery related to the present invention. It should be understood that the present invention may be applicable to other ocular surgery that requires eye fixation.

It is thought that the method and apparatus of the present invention will be understood from the foregoing description and that it will be apparent that various changes may be made in the form, construction, steps and arrangement of the parts and steps thereof, without departing from the spirit and scope of the invention or sacrificing all of their material advantages. The form herein described is merely a preferred or exemplary embodiment thereof.

What is claimed is:

1. An apparatus for restraining the movement of a human eye during ocular surgery, comprising:
   a shaft member having a longitudinal shaft axis, a shaft width dimension and a shaft height dimension, a distal end, and a proximal end;
   a single rod directly attached to said distal end of said shaft member, said rod for insertion through a side port incision in a peripheral cornea of an eye, and into an anterior chamber, said rod extending a rod length dimension, along a longitudinal first axis, in a first direction from said shaft member, said rod further having a rod width dimension, a rod height dimension, and a cross-sectional shape characteristic;
   a protrusion, having a shaft connection end, an opposing free end, and a protrusion width dimension, said protrusion directly attached to said shaft member at a location defined as being a first predetermined distance proximal of said first axis of said rod, and extending from said shaft member in a second direction and at a second predetermined distance from said shaft member, said second direction being opposite said first direction, said first distance being on the order of 2 mm. to be sufficiently short to inhibit penetration of said rod beyond the anterior chamber, said second distance being on the order of 1.2 mm., and said rod length dimension is on the order of 0.7 mm.;
   and said shaft width dimension, said rod width dimension and said protrusion width dimension being equal and constant along the lengths thereof.

2. An apparatus of claim 1 wherein said shaft is coupled to a handle connecting shaft which has a longitudinal handle connecting axis which is inclined between 0 and 90 degrees from said longitudinal shaft axis.

3. An apparatus of claim 2 wherein said handle connecting shaft, said shaft member, said single rod and said protrusion are burned from a single piece of surgical steel.

4. An apparatus of claim 2 wherein said handle connecting shaft, said shaft member, said single rod and said protrusion are formed from a single piece of titanium.

5. An apparatus of claim 2 wherein said handle connecting shaft is coupled to a handle which is substantially larger in width than said handle connecting shaft.

6. An apparatus of claim 5 wherein said handle is adapted and configured to be grasped by a human hand.

7. An apparatus of claim 6 wherein said handle has a handle longitudinal axis which is declined with respect to said longitudinal handle connecting axis by an angle between 0 and 90 degrees.

8. An apparatus of claim 7 wherein said handle longitudinal axis is substantially parallel with said longitudinal shaft axis.

9. An apparatus of claim 8 wherein said first direction is substantially orthogonal with respect to said longitudinal shaft axis.

10. An apparatus for restraining the movement of a human eye during ocular surgery, comprising:
    a shaft member having a longitudinal shaft axis, a shaft width dimension and a shaft height dimension, a distal end, and a proximal end;
    a single rod directly attached to said distal end of said shaft member, said rod for insertion through a side port incision in a peripheral cornea of an eye, and into an anterior chamber, said rod extending a rod length dimension, along a longitudinal first axis, in a first direction from said shalt member, said rod further having a rod width dimension, a rod height dimension, and a cross-sectional shape characteristic;
    a protrusion, having a shaft connection end, an opposing free end, and a protrusion width dimension, said protrusion directly attached to said shaft member at a location defined as being a first predetermined distance proximal of said first axis of said rod, and extending from said shaft member in a second direction and at a second predetermined distance from said shaft member, said second direction being orthogonal with respect to said longitudinal shaft axis, said first distance being on the order of 2 mm. to be sufficiently short to inhibit penetration of said rod beyond the anterior chamber, said second distance being on the order of 1.2 mm., and said rod length dimension is on the order of 7 mm.; and
    said shaft width dimension, said rod width dimension and said protrusion width dimension being equal and constant along the lengths thereof.

11. An apparatus of claim 10 wherein said first direction is on a first angle which is less than 90 degrees with respect to said longitudinal shaft axis.

12. An apparatus of claim 11 wherein said first angle is on the order of 45 degrees.

13. An apparatus of claim 12 wherein said shaft is coupled to a handle connecting shaft which has a longitudinal handle connecting axis which is inclined between 0 and 90 degrees from said longitudinal shaft axis.

14. An apparatus of claim 13 wherein said handle connecting shaft is coupled to a handle which is substantially larger in width than said handle connecting shaft.

15. An apparatus of claim 14 wherein said handle has a handle longitudinal axis which is declined with respect to said longitudinal handle connecting axis by an angle between 0 and 90 degrees.

16. An apparatus of claim 15 wherein said handle longitudinal axis is substantially parallel with said longitudinal shaft axis.

17. An apparatus for restraining the movement of a human eye during ocular surgery, comprising:
    a first eye gripping member having a proximal end and a distal end;
    a second eye gripping member having a proximal end and a distal end;

the proximal end of the first eye gripping member being joined to the proximal end of the second eye gripping member;

each of said eye gripping members comprising an arm having a proximal portion lying on one side of a longitudinal axis extending between the arms and a distal portion lying on the opposite side of the longitudinal axis, whereby converging pressure applied to said proximal portions causes the distal portions to diverge and thereby grip the cornea, and when the converging pressure is no longer applied to the proximal portions, the distal portions converge facilitating easy insertion and withdrawal through an eye incision;

each of said eye gripping members having a distal protuberance and a proximal protuberance attached to the distal portion of the arm, each of the protuberances attached directly to the corresponding arm by an attachment end and extending away from the arm to an opposite free end, the distance between the distal protuberance and the proximal protuberance being on the order of 1.5 mm., each of the protuberances having a height on the order of 0.25 mm.;

the protuberances of the first eye gripping member extending generally in a single first direction away from said longitudinal axis, and the protuberances of the second eye gripping member extending generally in a second direction opposite said first direction and away from said longitudinal axis.

* * * * *

UNITED STATES PATENT AND TRADEMARK OFFICE
CERTIFICATE OF CORRECTION

PATENT NO.   : 6,299,617 B1
DATED        : October 9, 2001
INVENTOR(S)  : John Stamler Page 1 of 1

It is certified that error appears in the above-identified patent and that said Letters Patent is hereby corrected as shown below:

Column 1,
Line 57, please delete "tom" and insert therefor -- torn --.

Column 3,
Line 9, please delete "I0" and insert therefor -- 10 --.

Column 5, claim 3,
Line 61, please delete "burned" and insert therefor -- formed --.

Column 6, claim 10,
Line 23, please delete "shalt" and insert therefor -- shaft --.
Line 39, please delete "7" and insert therefor -- .7 --.

Signed and Sealed this

Nineteenth Day of March, 2002

Attest:

Attesting Officer

JAMES E. ROGAN
Director of the United States Patent and Trademark Office